United States Patent
Lacey et al.

(10) Patent No.: US 9,519,069 B2
(45) Date of Patent: Dec. 13, 2016

(54) PRECISION SELF-ALIGNING CT DETECTOR SENSORS

(71) Applicant: General Electric Company, Schenectady, NY (US)

(72) Inventors: Joseph James Lacey, Cambridge, WI (US); Abdelaziz Ikhlef, Hartland, WI (US); Baiju Zacharia Babu, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 361 days.

(21) Appl. No.: 14/020,395

(22) Filed: Sep. 6, 2013

(65) Prior Publication Data

US 2015/0071401 A1 Mar. 12, 2015

(51) Int. Cl.
*A61B 6/00* (2006.01)
*G01T 7/00* (2006.01)
*G01N 23/04* (2006.01)
*G01T 1/16* (2006.01)
*A61B 6/03* (2006.01)

(52) U.S. Cl.
CPC .............. *G01T 7/005* (2013.01); *A61B 6/032* (2013.01); *A61B 6/4233* (2013.01); *G01N 23/046* (2013.01); *G01T 1/16* (2013.01)

(58) Field of Classification Search
CPC .................................................... A61B 6/4233
See application file for complete search history.

(56) References Cited

U.S. PATENT DOCUMENTS

| 6,982,423 | B2 * | 1/2006 | Elgali ................... G01T 1/1648 |
| | | | 250/370.11 |
| 7,190,759 | B2 * | 3/2007 | Ratzmann .............. A61B 6/035 |
| | | | 250/370.09 |
| 7,196,331 | B2 | 3/2007 | Heismann |
| 7,560,702 | B2 | 7/2009 | Meirav et al. |

(Continued)

FOREIGN PATENT DOCUMENTS

WO 2010058335 A2 5/2010

OTHER PUBLICATIONS

Search Report and Written Opinion from corresponding PCT application No. PCT/US2014/050510 dated Oct. 27. 2014; 9 pages.

*Primary Examiner* — David J Makiya
*Assistant Examiner* — Dani Fox
(74) *Attorney, Agent, or Firm* — Fletcher Yoder, P.C.

(57) ABSTRACT

CT detector modules are disclosed that include a module frame and a plurality of tileable detector sensors positioned on the module frame. Each of the tileable detector sensors includes an array of detector elements and a mounting structure directly or indirectly coupled to the detector elements to provide for a mounting and alignment of the detector sensor to the module frame. The mounting structure includes an alignment plate positioned generally opposite the array of detector elements, with the alignment plate having alignment pins forming a datum structure to align the detector sensor on the module frame and one or more threaded bosses configured to receive a fastener therein that secures the detector sensor to the module frame. The module frame includes keyed features that receive the alignment pins when the detector sensors are mounted on the module frame, so as to align the detector sensors on the module frame.

14 Claims, 11 Drawing Sheets

(56) References Cited

U.S. PATENT DOCUMENTS

| | | | |
|---|---|---|---|
| 7,564,940 B2 * | 7/2009 | Mattson | A61B 6/032 |
| | | | 250/370.09 |
| 7,606,346 B2 | 10/2009 | Tkaczyk et al. | |
| 2004/0131143 A1 * | 7/2004 | Pohan | 378/19 |
| 2005/0111612 A1 | 5/2005 | Ikhlef et al. | |
| 2005/0168993 A1 * | 8/2005 | Koegler et al. | 362/297 |
| 2008/0011950 A1 * | 1/2008 | Rose et al. | 250/339.03 |
| 2011/0080995 A1 | 4/2011 | Hoffman et al. | |
| 2011/0222659 A1 * | 9/2011 | Jorritsma | G01T 1/00 |
| | | | 378/62 |
| 2012/0183119 A1 * | 7/2012 | Ikhlef et al. | 378/19 |
| 2014/0064443 A1 * | 3/2014 | Kato | A61B 6/4429 |
| | | | 378/19 |

* cited by examiner

PRECISION SELF-ALIGNING CT DETECTOR SENSORS

BACKGROUND OF THE INVENTION

Embodiments of the invention relate generally to radiographic detectors for diagnostic imaging and, more particularly, to a computed tomography (CT) detector module having a plurality of tileable detector sensors having self-aligning features formed thereon.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are sent to the analog-to-digital convertors and then sent for processing into digital images.

In multi-slice imaging systems, parallel rows of detector modules—each consisting of a plurality of detector packs or sensors—are arranged so that data corresponding to each single array row can be used to generate a single thin slice image through a patient. The detector modules are generally positioned together in a side-by-side manner to form an arc that is essentially centered on the x-ray source. In positioning and affixing the detector modules to a gantry of the CT imaging system, it is recognized that such positioning and affixing of the detector modules must be done with great precision, making the manufacture of CT imaging systems very difficult and often requiring extensive testing, reworking and realignment of the detector modules before a CT imaging system of acceptable quality can be shipped to a customer.

Additionally, once a CT imaging system is in use in the field, the replacement of detector modules is difficult and time consuming. That is, in order to replace a defective radiation detector in a detector module, it is required that the entire module be removed and brought to a special offline fixture in order to swap a radiation detector, where a highly trained technician performs the replacement. In the field, use of such an alignment fixture is impractical and not desirable, as the fixture would need to be shipped to site without damage and, furthermore, an on-site field engineer would need to know how to use the fixture correctly and be able to verify alignment of the radiation detector post-installation. Alternatively, the entire module—which can consist of multiple detector sensors—must be replaced as a unit instead of just the defective sensor. As detector coverage increases, this issue becomes more expensive for the detector manufacturer to replace whole multi-sensor modules in the field.

Therefore, it would be desirable to design a CT detector that provides for self-alignment thereof without the need for special alignment fixtures or the skills of a highly trained installation technician. It would also be desirable for such a CT detector to have a tileable construction that enables ease of installation, scalability, early testability, and serviceability, with single sensor swapping/replacing being enabled rather than full, multi-sensor module swapping.

BRIEF DESCRIPTION OF THE INVENTION

In accordance with one aspect of the invention, a CT system includes a rotatable gantry having an opening to receive an object to be scanned, an x-ray projection source positioned on the rotatable gantry that projects a beam of x-rays toward the object, and a plurality of detector modules positioned on the rotatable gantry and configured to receive x-rays attenuated by the object. Each of the plurality of detector modules further includes a module frame having a top surface and side surfaces thereon and a plurality of tileable detector sensors positioned on the top surface of the module frame so as to receive the x-rays attenuated by the object, with each of the plurality of tileable detector sensors including an array of detector elements configured to receive x-rays attenuated through the object and convert the x-rays into electrical signals and a mounting structure directly or indirectly coupled to the array of detector elements and configured to provide for a mounting and alignment of the detector sensor to the module frame, the mounting structure comprising an alignment plate positioned on the detector sensor on a surface thereof generally opposite the array of detector elements. The alignment plate includes alignment pins forming a datum structure to align the detector sensor on the module frame and one or more threaded bosses configured to receive a fastener therein that secures the detector sensor to the module frame. The module frame includes keyed features formed therein that receive the alignment pins of each respective detector sensor therein when the detector sensors are mounted on the module frame, so as to align the detector sensors on the module frame.

In accordance with another aspect of the invention, a detector module for receiving x-rays attenuated by an object during a CT scan procedure includes a module frame comprising a top surface and side surfaces, and a plurality of tileable detector sensors positioned on the module frame to receive the x-rays attenuated by the object. Each of the plurality of detector sensors further includes an array of detector pixels configured to receive x-rays attenuated through the object and convert the x-rays into electrical signals and an alignment plate directly or indirectly coupled to the array of detector elements on a side thereof opposite from which the x-rays are received, with the alignment plate having alignment pins forming a datum structure to align the detector sensor on the module frame and one or more threaded bosses configured to receive a fastener therein that secures the detector sensor to the module frame. The module frame includes datum holes formed therein that receive the alignment pins of each respective detector sensor therein when the detector sensors are mounted on the module frame, so as to align the detector sensors on the module frame.

In accordance with yet another aspect of the invention, a detector module for receiving x-rays attenuated by an object during a CT scan procedure includes a module frame and a plurality of selectively addable detector sensors positioned on the top surface of the module frame so as to receive the x-rays attenuated by the object. Each of the plurality of detector sensors further includes an array of detector elements configured to receive x-rays attenuated through the object and convert the x-rays into electrical signals and an alignment plate positioned on the detector sensor on a surface thereof generally opposite the array of detector elements, the alignment plate including alignment pins forming a datum structure to align the detector sensor on the module frame. The module frame includes datum holes formed therein that receive the alignment pins of each respective detector sensor therein when the detector sensors are mounted on the module frame, so as to align the detector sensors on the module frame.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a 256 slice computed tomography (CT) system. However, as will be explained in detail below, the invention is equally applicable for use with other single and multi-slice configurations (i.e., any modular-based detector that can be assembled to have a desired size). Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
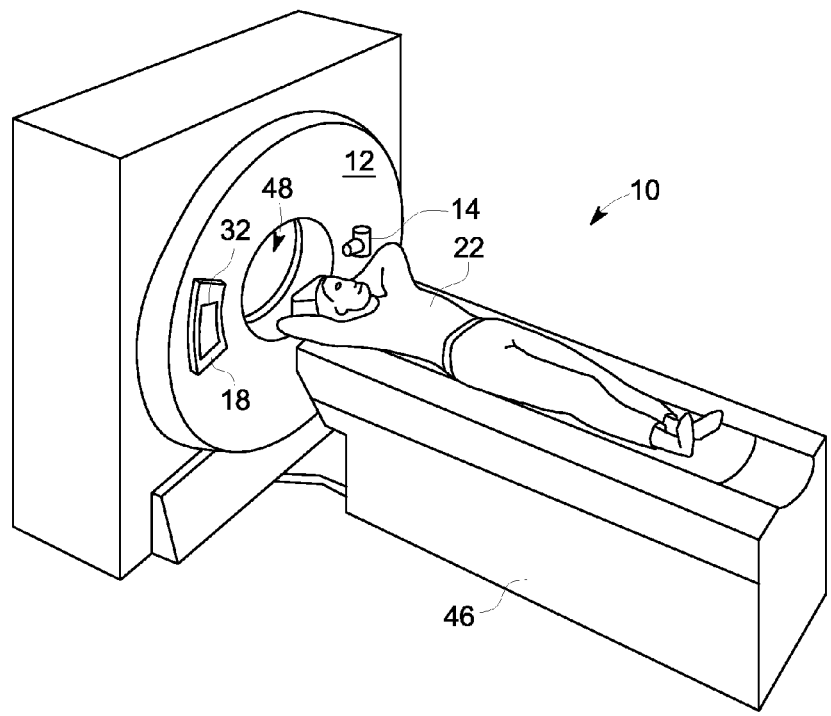
FIG. 1 is a pictorial view of a CT imaging system.
Figure 2:
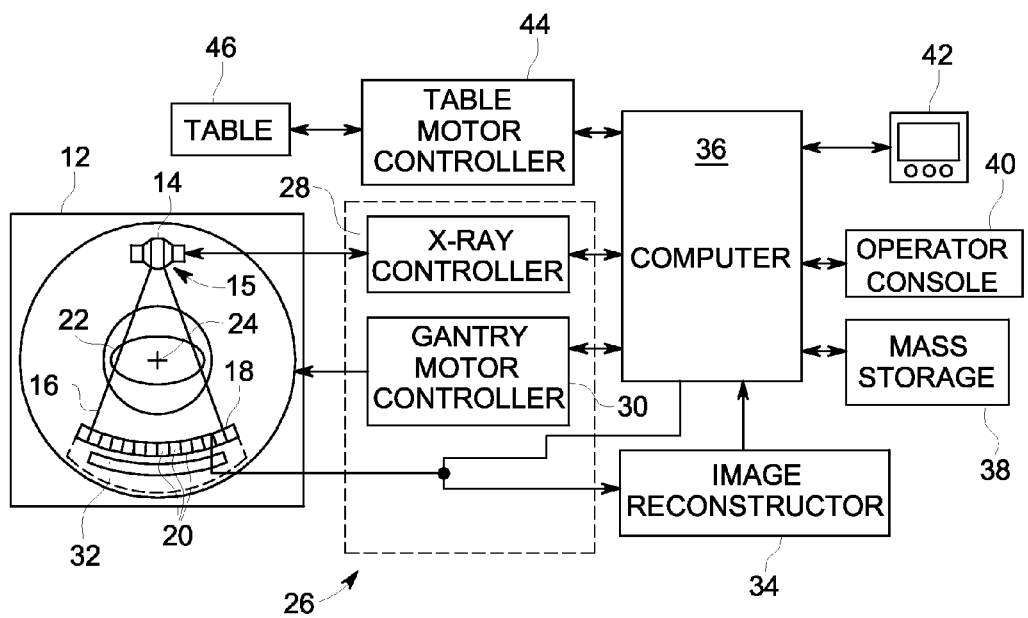
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays from a focal spot 15 of the source 14 and toward a detector assembly 18 on the opposite side of the gantry 12. Referring now to FIG. 2, detector assembly 18 is formed by a plurality of detector modules 20 and a control and processing board 32 (i.e., electronics board). The plurality of detector modules 20 sense the projected x-rays 16 that pass through a medical patient 22, with the electronics board 32 performing subsequent processing on the acquired data. Each detector module 20 produces an output that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from electronics board 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to electronics board 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
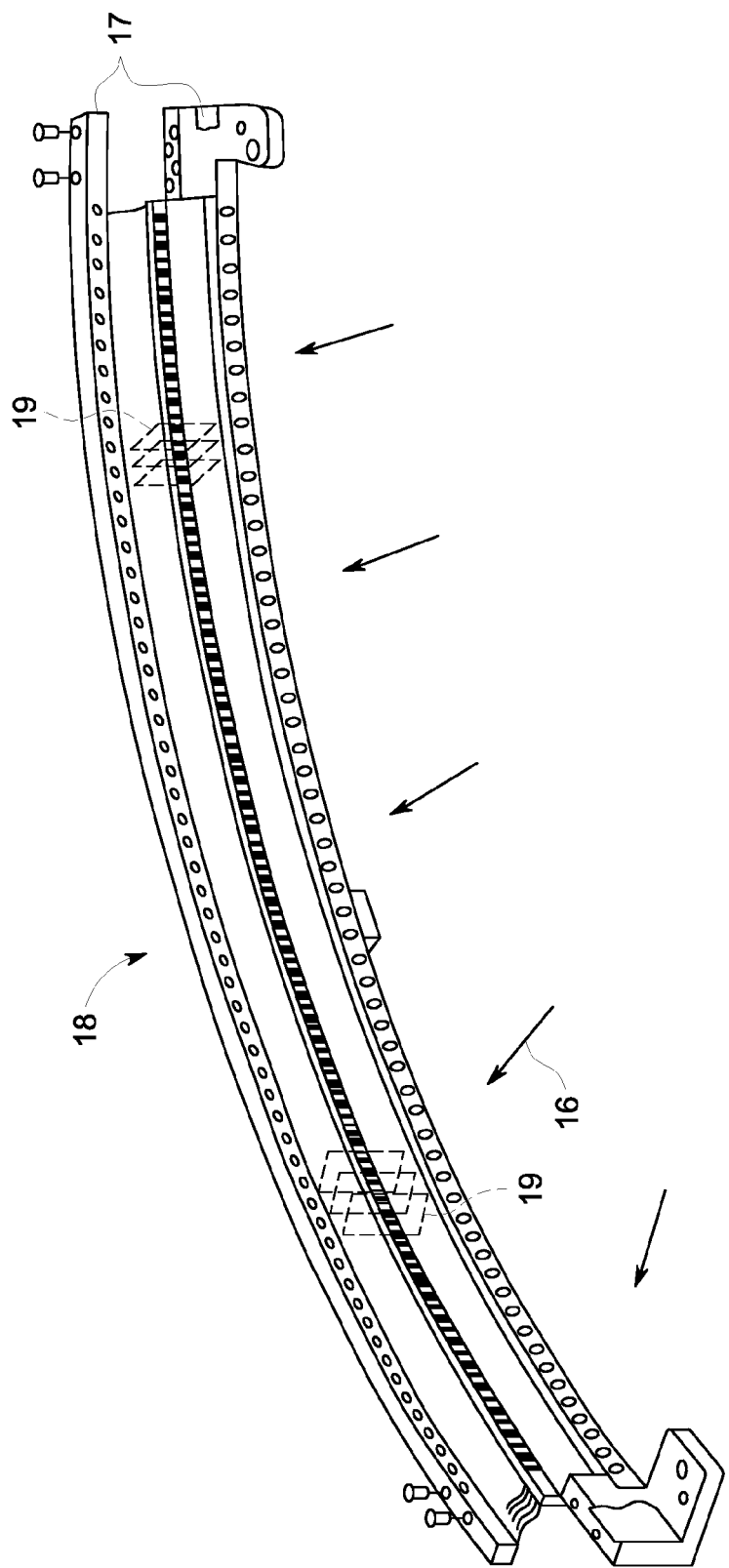
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays and remove scatter x-ray 16 before such beams impinge upon, for instance, detector module 20 of FIG. 4 positioned on detector assembly 18. According to an embodiment of the invention, detector assembly 18 includes 57 detector modules 20, each detector module 20 having an array size of 256×16 of pixel elements. As a result, detector assembly 18 has 256 rows and 912 columns (16×57 detectors), which allows 256 simultaneous slices of data to be collected with each rotation of gantry 12. However, while an exemplary detector module 20 is set forth as having an array size of 256×16 of pixel elements, it is recognized that the number of rows and columns in detector assembly 18 can be selectively controlled based on the structure of detector modules 20 according to embodiments of the invention, such that the number of slices simultaneously collected can be lesser or greater in number, such as up to 512 slices of data.

Figure 4:
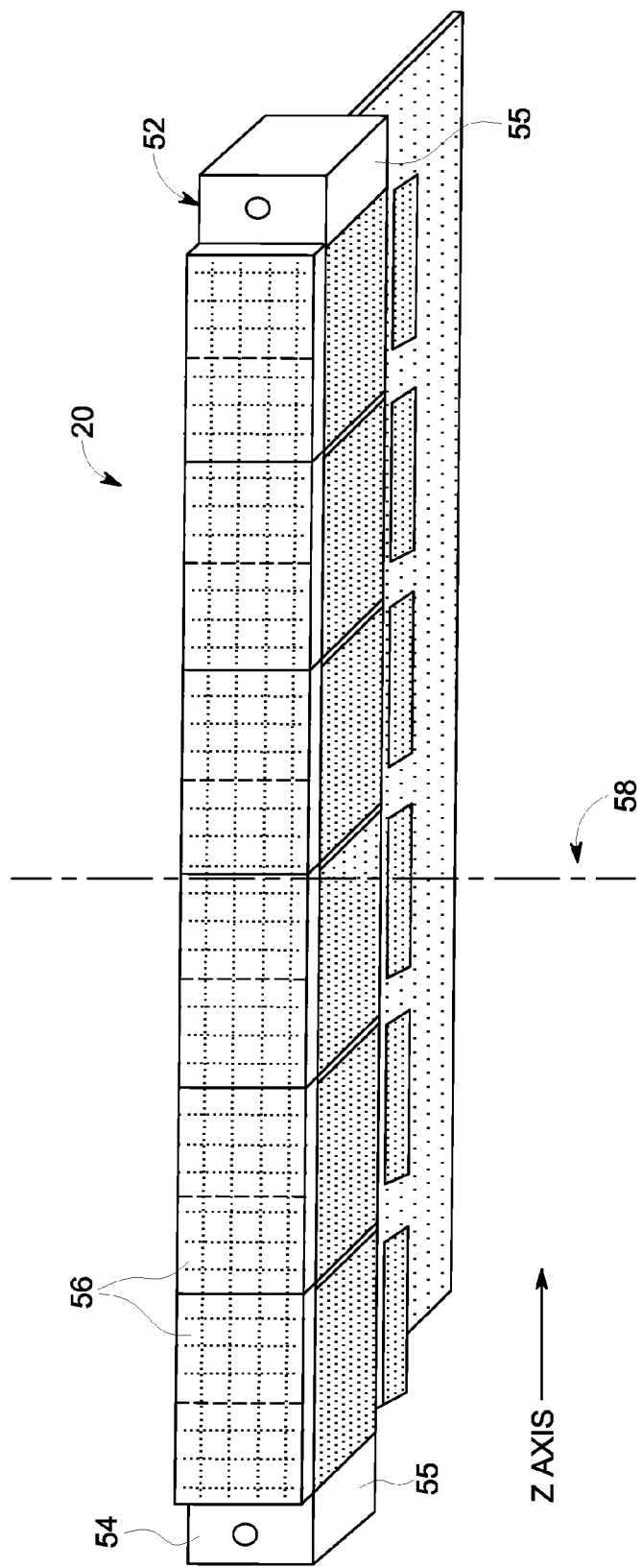
FIG. 4 is a perspective view of a detector module according to an embodiment of the invention.

Referring to FIG. 4, construction of a detector module 20 is shown according to an exemplary embodiment of the invention. The detector module 20 includes a module frame 52 having a top surface 54 and side surfaces 55 thereon. According to embodiments of the invention, top surface 54 can be constructed as a flat surface, an approximated curve formed in a circular arc net following or not following the arc of the x-ray beam, or a stepped configuration with a plurality of angled facets thereon. As shown in FIG. 4, a plurality of detector sub-modules or "sensors" 56 are positioned onto top surface of module frame 52 and aligned along the Z-axis to receive and process x-rays that attenuate through a patient or object. According to embodiments of the invention, the number of detector sensors 56 positioned on top surface 54 of module frame 52 can be controlled during a manufacturing process based on the operating requirements of detector modules 20 in the CT system 10 (FIG. 1). That is, the detector sensors 56 of detector module 20 are configured as tileable detector sensors, in that detector sensors 56 can be selectively added to module frame 52 as desired such that the number of detector sensors 56 included in detector module 20 can be controlled, so as to vary the amount of coverage along the Z-axis (i.e., vary/control the number of slices acquired). Thus, for example, according to one embodiment of the invention, six detector sensors 56 may be included in detector module 20. However, other embodiments of detector module 20 could include four, eight, or twelve detector sensors 56, for example, as indicated by the phantom lines shown in FIG. 4. In each embodiment, the detector sensors 56 are positioned on top surface 54 in a symmetrical fashion about a centerline 58 of the detector module along the Z-axis. Thus, based on a populating and depopulating of detector sensors 56 on module frame 52, it is recognized that a detector module 20 can be built having a controllable length/coverage along the Z-axis.

Figure 5:
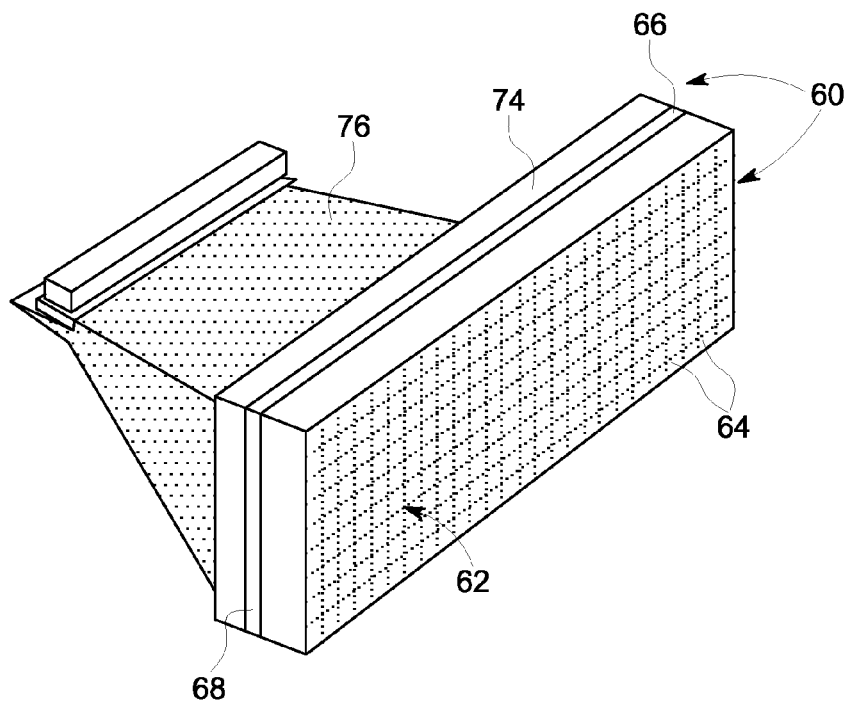
FIGS. 5 and 6 are views of a detector sensor for use with the detector module of FIG. 4 according to an embodiment of the invention.
Figure 6:
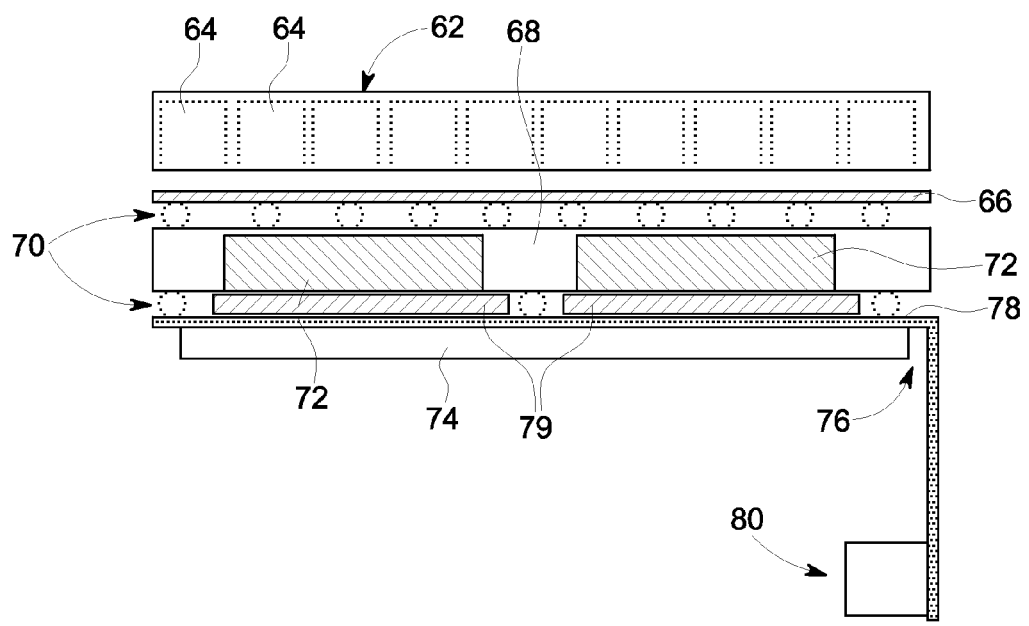

A detailed view of a detector sensor 56 is shown in FIGS. 5 and 6 according to an embodiment of the invention. Detector sensor 56 includes an array of detector elements or pixels 60 that are configured to receive x-rays attenuated through the object and convert the x-rays into analog electrical signals. According to one embodiment, the detector elements/pixels 60 are formed from a scintillator-photodiode pair. In forming the scintillator-photodiode pair, a number of scintillator detector elements or pixels 62 are arranged to form a scintillating pack array 64. For example, a scintillating pack array 64 may be composed of a 32×16 array of scintillator detector elements 62, such that each scintillating pack array 64 includes 32 slices. The scintillating pack array 64 is positioned on a photodiode array 66 formed of a plurality of diode elements or pixels (not shown), with the diode array 66 being formed of a 32×16 array of diodes, for example, that corresponds to the number of scintillator detector elements 62.

As shown in FIGS. 5 and 6, scintillator detector elements 62 are optically coupled to diode array 66 and diode array 66 is in turn electrically coupled to one or more application specific integrated circuit (ASIC) electronics packages 68. The ASIC electronics package 68 (i.e., analog-to-digital (A/D) convertor) is electrically and mechanically coupled to diode array 66 by way of an input/output (I/O) interconnect 70 formed thereon (i.e., on front and back surfaces of the ASIC electronics package 68). The I/O interconnect 70 may be formed as a ball grid array (BGA) type interconnect, for example, or another similar bonding device that electrically and mechanically couples the ASIC electronics package 68 to diode array 66. According to embodiments of the invention, each ASIC electronics package 68 includes one or more individual ASIC dies 72, such as four ASIC dies 72, that collectively form the package 68.

While detector sensor 56 is described above as including a scintillator array 64 positioned on a photodiode array 66, it is recognized that embodiments of the invention also encompass direct conversion sensors. That is, while detector sensor 56 is shown in FIGS. 5 and 6 as including scintillator array 64 and photodiode array 66, it is recognized that such elements/materials in detector sensor 56 could be replaced with a direct conversion material that directly converts x-rays into electrical signals, such as cadmium-telluride (CdTe) or cadmium-zinc-telluride (CZT). It is further recognized that sensors designs that differ from that shown in FIGS. 5 and 6 are also considered to be within the scope of the invention.

According to embodiments of the invention, ASIC electronics package(s) 68 is configured, in part, to perform analog-to-digital (A/D) conversion of signals received from photodiode array 66. That is, ASIC electronics package 68 functions to convert analog electrical signals received from photodiode array 66 into digital numbers based on a level of the signal received from the diode array. Thus, in the operation of one embodiment, x-rays impinge within scintillator detector elements 62 to generate photons that traverse pack array 64 and are detected on a photodiode pixel/element within diode array 66, with an analog signal generated by diode array 66 responsive thereto being received by ASIC electronics package(s) 68 for conversion to a digital signal/number.

As further shown in FIGS. 5 and 6, a substrate layer 74 (i.e., ASIC package substrate) is positioned beneath ASIC electronics package(s) 68 and opposite from scintillating pack array 64. The substrate layer 74 is formed of an electrically insulating material, such as a multi-layer ceramic (MLC), and is configured to provide support/rigidity to detector sensor 56. Positioned between substrate layer 74 and ASIC electronics package(s) 68 is a flex circuit 76 attached to ASIC electronics package 68 that routes signals from the ASIC electronics package to control and processing board 32 of the detector module 20 (FIG. 4), and also transfers controls and power to/from the control and processing board 32. The flex circuit 76 is in the form of a "digital flex circuit" in that it functions to transmit digital signals/numbers from the ASIC electronics package 68. The flex circuit 76 includes a connector/electrically bondable area 78 configured to interface with ASIC electronics packages 68 (i.e., interface with I/O interconnect 70) and a connector 80 configured to interface with control/processing board 32 of the detector module 20 (FIG. 4). According to one embodiment, connector/electrically bondable area 78 of flex circuit 76 has holes formed therein (not shown) that correspond to the ASIC dies in ASIC electronics package 68 to thermally bond the substrate layer 74 (via pedestals) to the ASIC electronics package 68. Also, according to an embodiment, a thermal adhesive 79 is also provided between ASIC electronics package 68 and flex circuit 76 to bond the components together, as well as provide a separate thermal interface for detector sensor 56.

Further benefits are provided by the structure and inclusion of detector sensors 56 in detector module based on the controllable and variable nature of detector sensors, both with regard to the tileability and sizing of detector sensors. That is, according to embodiments of the invention, the configuration of detector sensor 56 can be varied in order to optimize for performance and scalability. That is, while a detector sensor 56 is described above as having an array of 32×16 detector pixels/elements (i.e., 32 slices and 16 channels), it is recognized that the detector sensor 56 may be formed so as to have any one of a number of N×M arrays of pixels/elements (e.g., N=16, 32, or 64, M=16, 24, or 32, for example), with the size of the array being optimized based on cost, performance, yield, testing time scalability, reliability, etc. Correspondingly, the dimensions of the detector sensor 56 may vary, with the detector sensor 56 having a length (i.e., dimension along the Z-axis) from 10 mm in length up to 40 mm in length depending on the exact configuration of detector module 20.

According to embodiments of the invention, each of the detector sensors 56 is further constructed with self-aligning features that enable plugging of the sensors into a frame (e.g., frame 52, FIG. 4) having matching keyed features. The self-aligning features create alignment datum surfaces for detector sensors that enable placement of the sensors with such precision that no fixturing or adjustment is required. Factory and field swapping of individual detector sensors can be performed by way of the self-aligning features without the use of specialty fixtures or tools with precision alignment, such that true plug-and-play detector sensor capability is provided.

Figure 7:
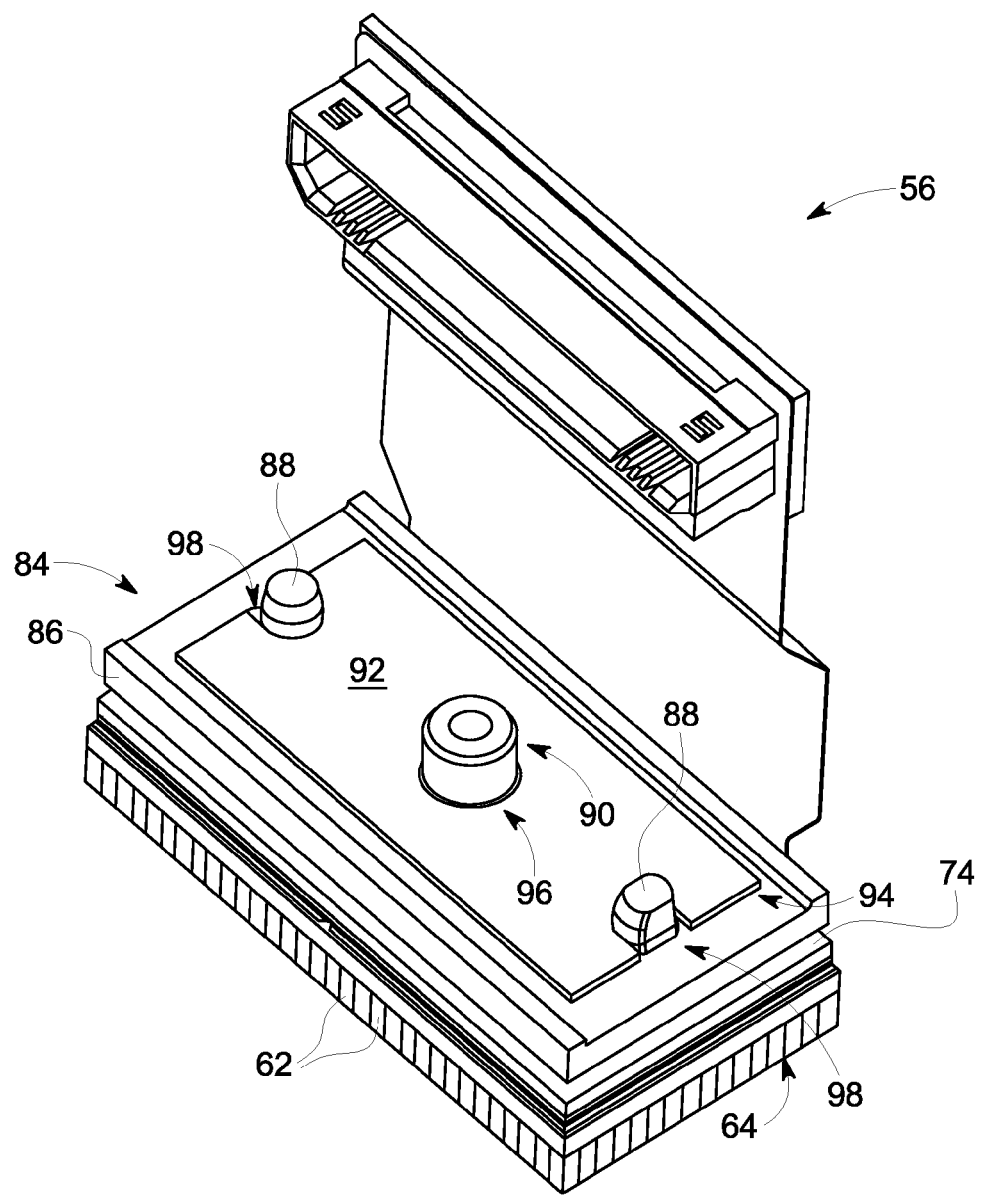
FIG. 7 is a perspective view of the detector sensor of FIGS. 5 and 6 incorporating a vertical mounting structure with self-aligning features according to an embodiment of the invention.
Figure 8A:
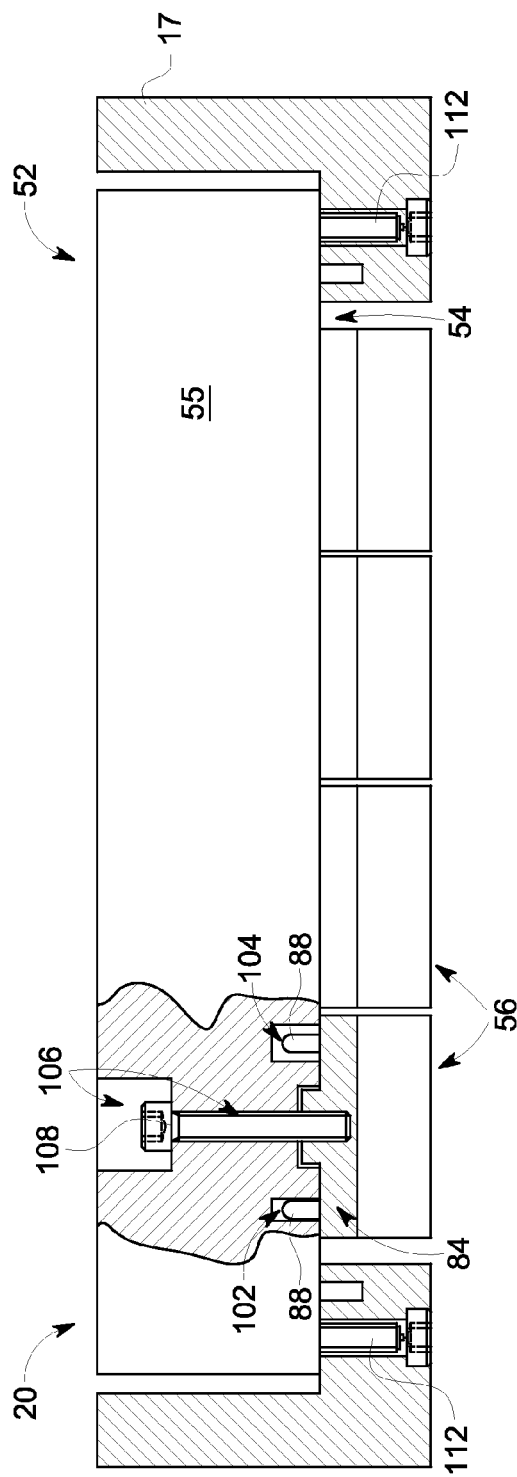
FIGS. 8A and 8B are views of the detector sensor of FIG. 7 mounted on a module frame by way of the vertical mounting structure according to an embodiment of the invention.
Figure 8B:
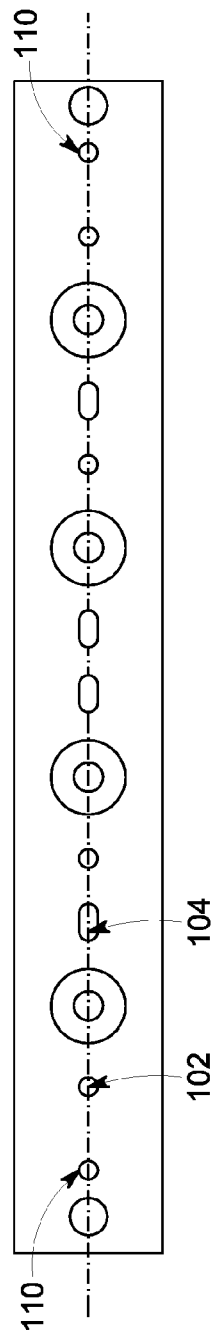

Referring now to FIG. 7 and FIGS. 8A and 8B, views of a detector sensor 56 including self-aligning features, and of the mating of such detector sensors to a corresponding module frame 52 to collectively form a detector module 20, are shown according to an embodiment of the invention. Referring first to FIG. 7, a detector sensor 56 is shown that includes what is generally referred to herein as a "vertical" mounting structure 84 formed thereon that provides an alignment datum feature thereon that enables precision placement of the detector sensor onto a frame. The vertical mounting structure 84 includes an alignment plate 86 that is permanently attached to the detector sensor 56 on a side of the detector structure opposite the scintillating pack array 64 (i.e., opposite from a side at which x-rays are received), with the alignment plate 86 being precision aligned to the scintillating pack array 64. According to one embodiment, the alignment plate is affixed to the substrate layer 74 on the back of the detector sensor 56, such as by way of an adhesive, for example, or other suitable material. The alignment plate 86 is formed as a generally planar structure that is oriented parallel to the main components of the detector sensor 56 (i.e., scintillating pack array 64, photodiode array 66).

The alignment plate 86 includes alignment pins 88 formed thereon that extend outwardly from the plate to provide for the self-alignment of the detector sensor 56 onto a corresponding module frame 52 (FIG. 4). That is, the alignment pins 88 serve as a datum structure that provides for self-alignment of the detector sensor 56 onto a corresponding module frame 52, as the alignment pins 88 are configured to mate with matching keyed features formed in the module frame 52 that receive the alignment pins 88 to create an aligned assembly, as will be explained in greater detail below. While two alignment pins 88 are shown as being formed on generally opposing ends of alignment plate 86, it is recognized that a greater number of alignment pins 88 could be formed thereon to serve as a datum structure.

The alignment plate 86 also includes a mating feature 90 formed thereon that is configured to provide for attachment of the vertical mounting structure 84 (and the detector sensor 56) onto a module frame 52. According to an exemplary embodiment, the mating feature 90 is formed as a threaded boss formed in a central region of the alignment plate 86, with the threaded boss 90 providing secure attachment of the detector sensor 56 to the module frame 52 when a respective screw is received by the threaded boss 90.

According to an exemplary embodiment, the vertical mounting structure 84 also includes a thermal gap pad 92 positioned on the alignment plate 86 so as to be between the alignment plate 86 and the module frame 52 to which the detector sensor 56 is to be mounted. The thermal gap pad 92 is positioned in a recessed pocket 94 formed in the alignment plate that enables addition of the thermal gap pad 92. The recessed pocket 94 is precision machined such that, when a detector sensor 56 is secured to the module frame 52, a consistent low variation thermal interface (due to consistent levels of gap pad compression) with low thermal resistance is formed via the thermal gap pad 92. Consistent low thermal resistance is required to enable precision temperature control of the detector sensor 56—and inclusion of the thermal gap pad 92 provides the ability to deal with and control the thermal contact resistance between sensor 56 and frame 52. According to embodiments of the invention, the thermal gap pad 92 may be formed of any of a number of suitable thermal interface materials (TIMs). Examples of suitable TIMs include, without limitation, adhesives, greases, gels, pads, films, liquid metals, compressible metals, and phase change materials. Compressible metals, for example, are sufficiently soft to make intimate contact between adjoining surfaces and may include, for example, indium. As shown in FIG. 7, according to one embodiment, the thermal gap pad 92 includes an opening 96 and a pair of notches 98 formed therein/therethrough that accommodate the threaded boss 90 and alignment pins 88, respectively, of the alignment plate 86.

As shown in FIGS. 8A and 8B, a plurality of detector sensors 56 are positioned on the module frame 52, with each detector sensor 56 being aligned to the module frame 52 and secured thereto by way of the vertical mounting structure 84 provided on each detector module 56. As indicated previously above, the module frame 52 includes keyed features formed therein that match the datum alignment pins 88 formed on the vertical mounting structure 84, that receive the alignment pins 88 when a detector sensor 56 is positioned on the module frame 52. As shown in FIGS. 8A and 8B, a datum hole 102 and datum slot 104 are formed in the module frame 52 for each respective detector sensor 56 that is to be mounted on the module frame 52, with the alignment pins 88 being received in the hole 102 and slot 104 so as to enable self-alignment of a detector sensor 56 that is placed on the module frame 52. When a detector sensor 56 is plugged into the module frame 52, its position is thus set and not adjustable.

To provide for securing of a respective detector sensor 56 to the module frame 52, a threaded opening 106 is formed through the module frame 52 between a respective datum hole-datum slot pair 102, 104, with the threaded opening 106 extending out to top surface 54 of the module frame 52. As shown in FIG. 8A, threaded opening 106 receives a fastener 108 therein (e.g., screw) that extends through the module frame 52 so as to be received in the mating feature (i.e., threaded boss) 90 of the vertical mounting structure 84 affixed to detector sensor 56. The fastener 108 can be tightened to secure the detector sensor 56 to module frame 52, with the tightening of the fastener 108 also providing consistent compression of the thermal gap pad 92 of the vertical mounting structure 84, such that the overall contact resistance (as well as variation in resistance) between the detector sensor 56 and module frame 52 is controlled and a consistent low variation thermal interface with low thermal resistance is formed via the thermal gap pad 92.

As further shown in FIGS. 8A and 8B, module frame 52 includes features thereon for aligning and mating the frame with the rails 17 of detector assembly 18 (FIG. 3). The module frame 52 includes a rail datum location hole 110 that mates with a corresponding feature on the rail 17, such that the frame of detector module 20 is self-aligned with the rails 17. A mating feature 112 is also provided on module frame 52 for securing the frame to the rails 17.

Figure 9A:
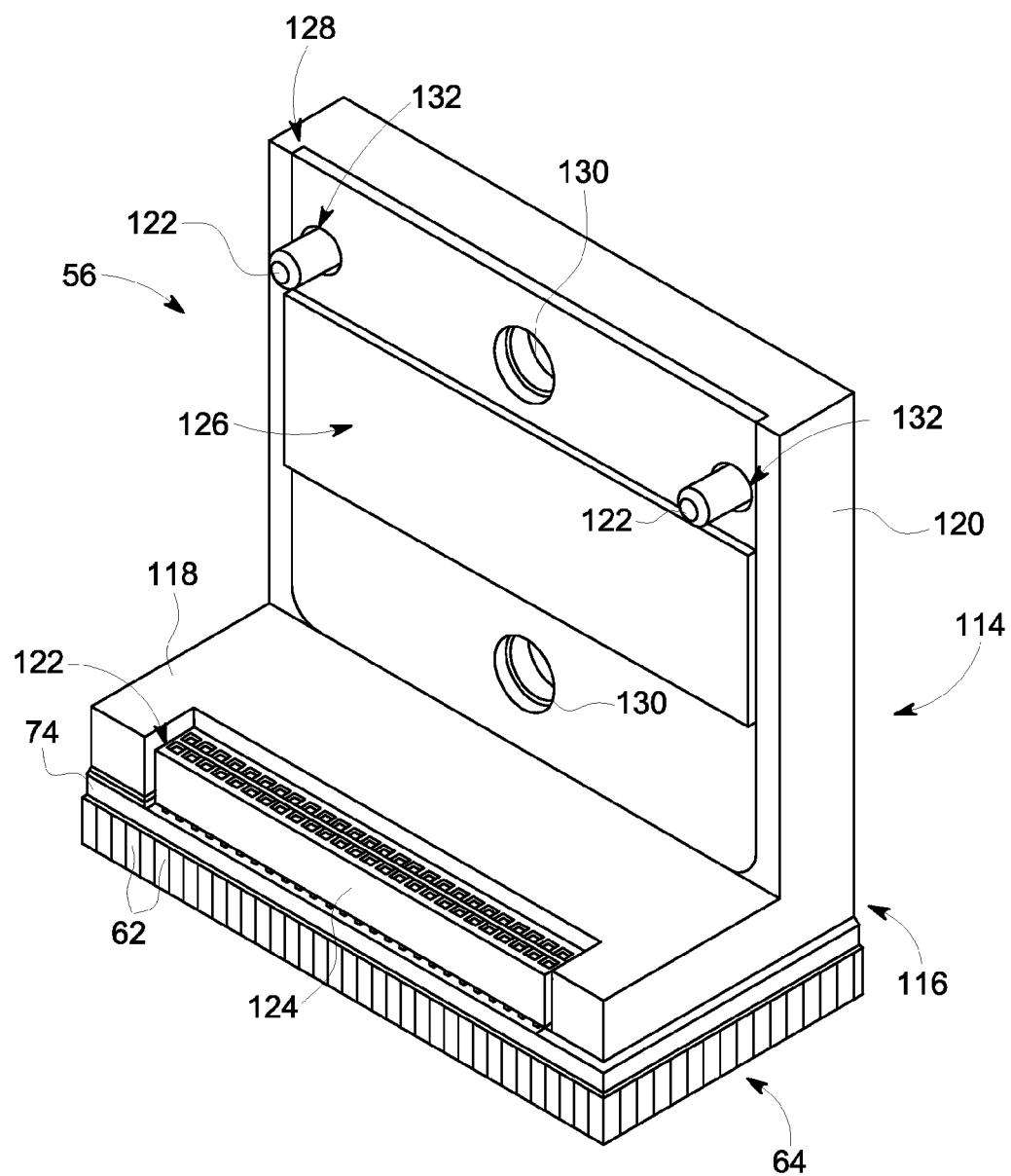
FIGS. 9A and 9B are perspective views of the detector sensor of FIGS. 5 and 6 incorporating a horizontal mounting structure with self-aligning features according to an embodiment of the invention.
Figure 9B:
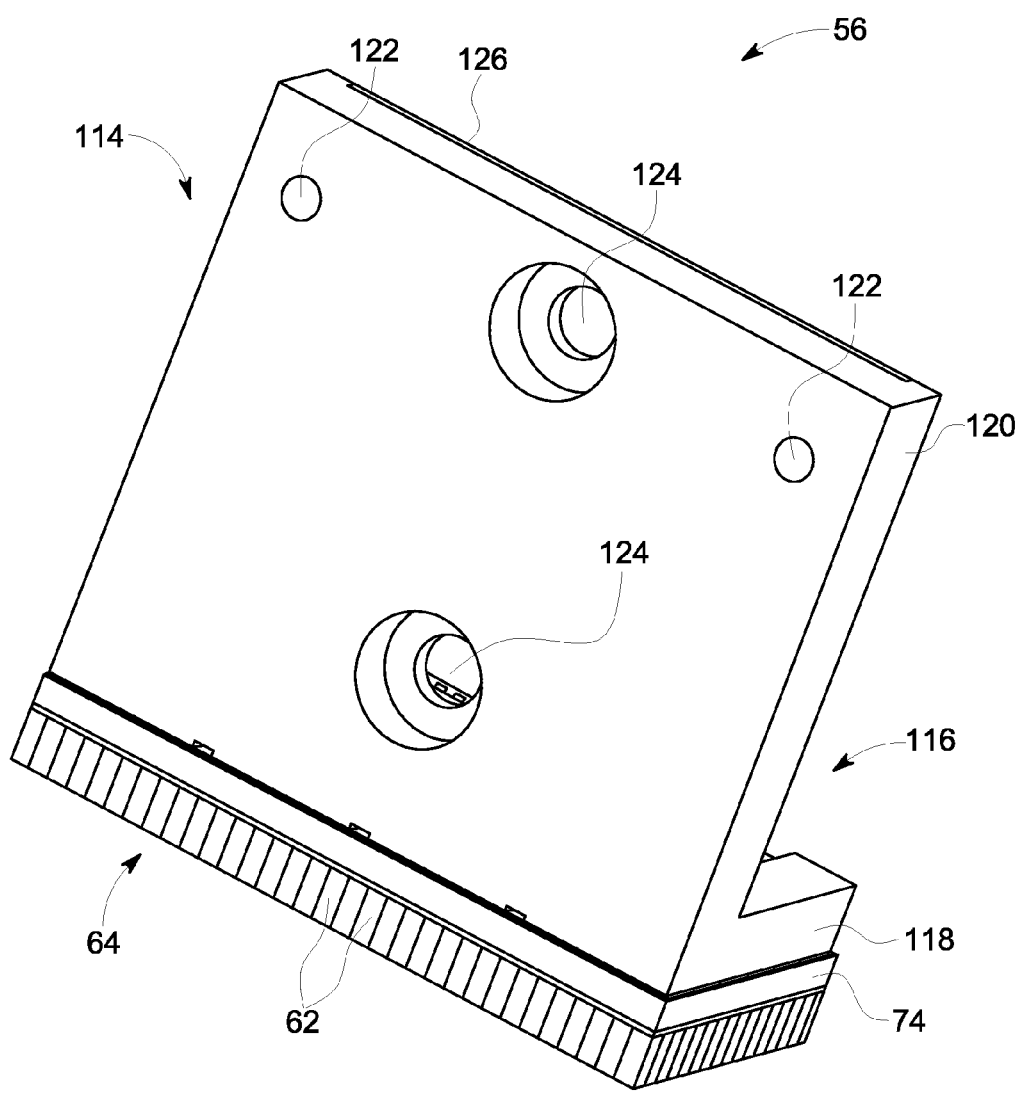

Referring now to FIGS. 9A and 9B and FIGS. 10A and 10B, views of a detector sensor 56 including self-aligning features, and of the mating of such detector sensors 56 to a corresponding module frame 52, are shown according to another embodiment of the invention. Referring first to FIGS. 9A and 9B, a detector sensor 56 is shown that includes what is generally referred to herein as a "horizontal" mounting structure 114 formed thereon that provides an alignment datum feature thereon that enables precision placement of the detector sensor 56 onto a frame. The horizontal mounting structure 114 includes an L-shaped alignment plate 116 having a lower member 118 oriented parallel to the main components of the detector sensor 56 (i.e., scintillating pack array 64, photodiode array 66) and a lengthwise member 120 extending perpendicularly outward from the lower member 118. The L-shaped alignment plate 116 is permanently attached to the detector sensor 56 on a side of the detector structure opposite the scintillating pack array 64, with the bottom member 118 of L-shaped alignment plate 116 being precision aligned to the scintillating pack array 64. According to one embodiment, the bottom member 118 is affixed to the substrate layer 74 on the back of the detector sensor 56, such as by way of an adhesive, for example, or other suitable material. Additionally, according to one embodiment, the bottom member 118 includes a cut-out 122 formed thereon that provides for attachment of the horizontal mounting structure 114 to detector sensor 56 by accommodating an SMT digital connector 124 of the detector sensor 56 that extends out the backside thereof. It is recognized, however, that L-shaped alignment plate 116 could include a bottom member 118 that does not have a cut-out 122 formed therein, such as when detector sensor 56 includes a direct flex attach 76, such as is shown in FIGS. 5 and 6.

As shown in FIGS. 9A and 9B, the lengthwise member 120 of L-shaped alignment plate 116 includes alignment pins 122 formed thereon that extend outwardly from the lengthwise member 120 (on a side to be mated to a module frame 52) to provide for the self-alignment of the detector sensor 56 onto a corresponding module frame. That is, the alignment pins 122 serve as a datum structure that provides for self-alignment of the detector sensor 56 onto a corresponding detector module frame 52, as the alignment pins 122 are configured to mate with matching keyed features formed in the module frame 52 that receive the alignment pins 122 to create an aligned assembly. While two alignment pins 122 are shown as being formed on generally opposing ends of lengthwise member 120 of L-shaped alignment plate 116, it is recognized that a greater number of alignment pins 122 could be formed thereon to serve as a datum structure.

The L-shaped alignment plate 116 also includes mating features 124 formed thereon that are configured to provide for attachment of the horizontal mounting structure 114 (and the detector sensor 56) onto a module frame 52. According to an exemplary embodiment, the mating features 124 are formed as threaded bosses formed in the lengthwise member 120 of L-shaped alignment plate 116, with the threaded bosses 124 providing for secure attachment of the detector sensor 56 to the module frame 52 when respective fasteners or screws are received by the threaded bosses 124.

According to an exemplary embodiment, the horizontal mounting structure 114 also includes a thermal gap pad 126 positioned on the lengthwise member 120 of the L-shaped alignment plate 116 so as to be between the alignment plate 116 and the module frame 52 to which the detector sensor 56 is to be mounted. The thermal gap pad 126 is positioned in a recessed pocket 128 formed in the lengthwise member 120 that enables addition of the thermal gap pad 126. The recessed pocket 128 is precision machined such that, when a detector sensor 56 is secured to the module frame 52, a consistent low variation thermal interface (due to consistent levels of gap pad compression) with low thermal resistance is formed via the thermal gap pad 126. Consistent low thermal resistance is required to enable precision temperature control of the detector sensor 56—and inclusion of the thermal gap pad 126 provides the ability to deal with and control the thermal contact resistance between sensor 56 and frame 52. According to embodiments of the invention, the thermal gap pad 126 may be formed of any of a number of suitable thermal interface materials (TIMs). Examples of suitable TIMs include, without limitation, adhesives, greases, gels, pads, films, liquid metals, compressible metals, and phase change materials. Compressible metals, for example, are sufficiently soft to make intimate contact between adjoining surfaces and may include, for example, indium. As shown in FIGS. 9A and 9B, according to one embodiment, the thermal gap pad 126 includes a pair of openings 130 and a pair of holes 132 formed therein/therethrough that are aligned with the threaded bosses 124 and that accommodate the alignment pins 122, respectively, of the lengthwise member 120 of the L-shaped alignment plate 116.

Figure 10A:
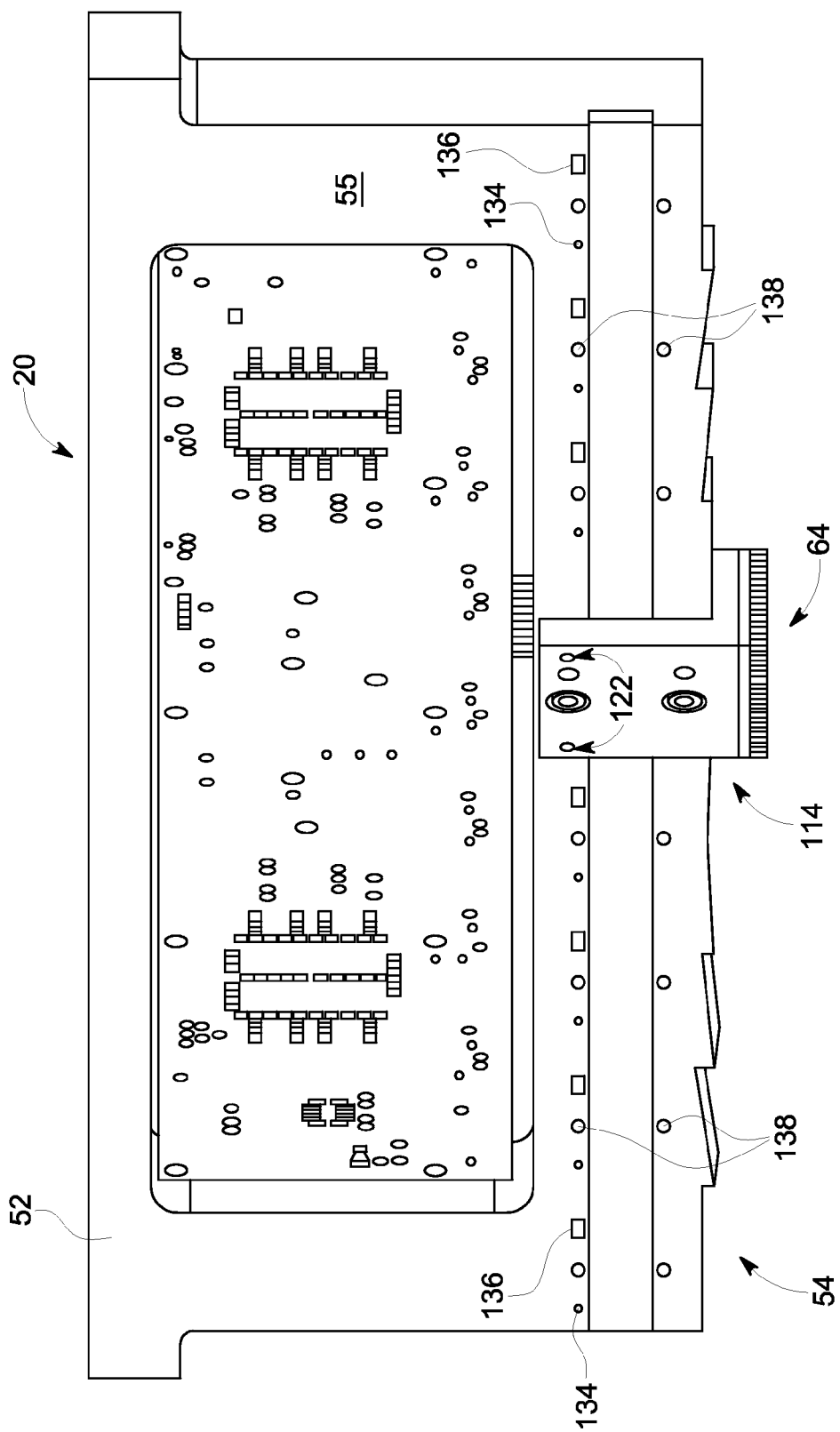
FIGS. 10A and 10B are views of the detector sensor of FIGS. 9A and 9B mounted on a module frame by way of the horizontal mounting structure according to an embodiment of the invention.
Figure 10B:
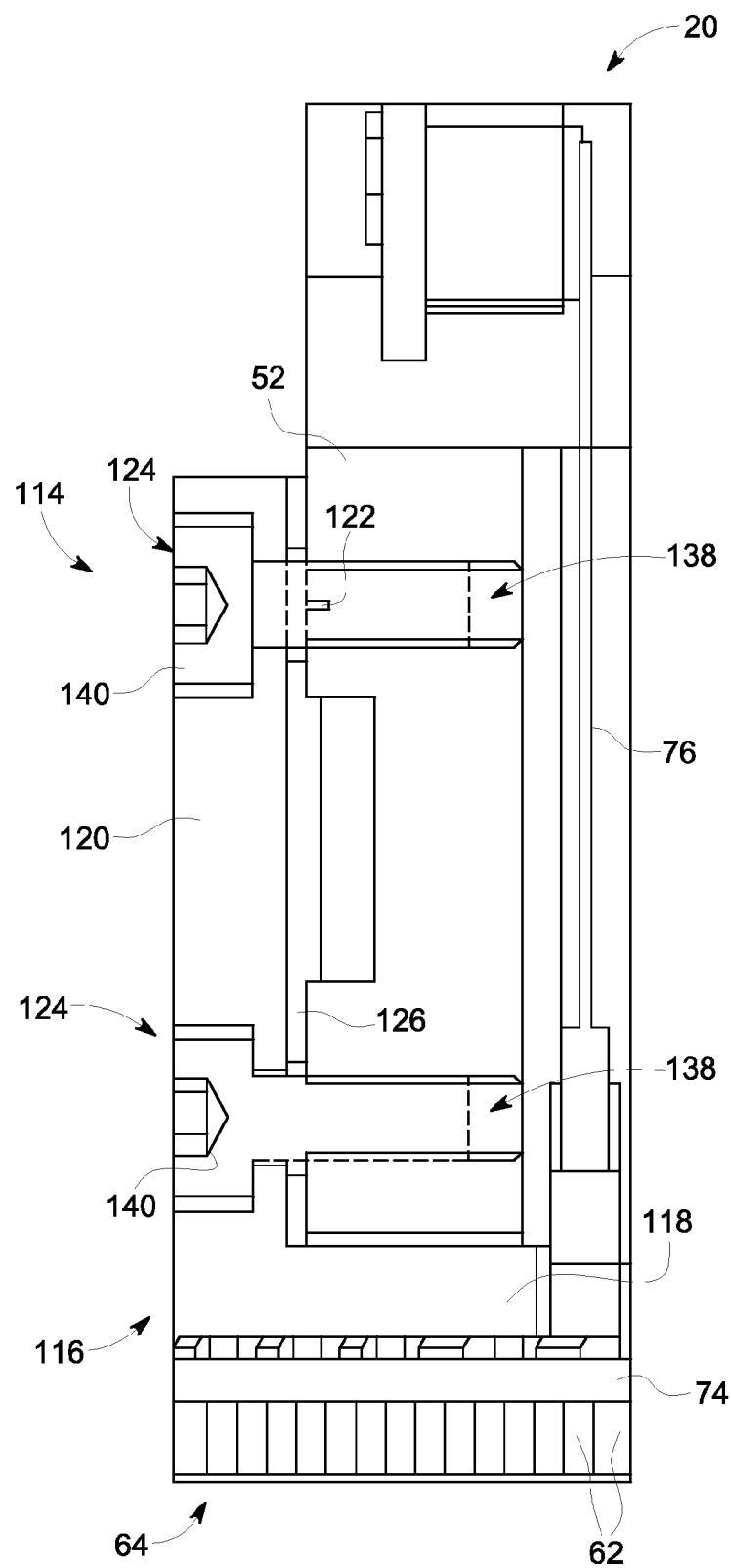

A mating of a detector module 56 to a module frame 52 by way of a horizontal mounting structure 114 is shown in FIGS. 10A and 10B, according to an embodiment of the invention. As indicated previously above, the module frame 52 includes keyed features (i.e., datum openings) formed therein that match the datum alignment pins 122 formed on the horizontal mounting structure 114, that receive the alignment pins 122 when a detector sensor 56 is positioned on the module frame 52. As shown in FIG. 10, a datum hole 134 and datum slot 136 are formed in the module frame 52 on a side surface 55 thereof for each respective detector sensor 56 that is to be mounted on the module frame 52, with the alignment pins 122 being received in the hole and slot 134, 136 so as to enable self-alignment of a detector sensor 56 that is placed on the module frame 52. When a detector sensor 56 is plugged into the module frame 52, its position is thus set and not adjustable.

To provide for securing of a respective detector sensor 56 to the module frame 52, threaded openings 138 are formed in a side surface 55 of the module frame 52 between a respective datum hole-datum slot pair 134, 136. As shown in FIG. 10B, threaded openings 138 receive fasteners 140 therein (e.g., screws) that extend through the mating features (i.e., threaded bosses) 124 of alignment plate 116 so as to be received in the threaded openings 138 formed in the module frame 52. The fasteners 140 can be tightened to secure the detector sensor 56 to module frame 52, with the tightening of the fasteners 140 also providing consistent compression of the thermal gap pad 126 of the horizontal mounting structure 114, such that the overall contact resistance (as well as variation in resistance) between the detector sensor 56 and module frame 52 is controlled and a consistent low variation thermal interface with low thermal resistance is formed via the thermal gap pad 126. According to another embodiment, a stud (not shown) from the alignment plate 116 could be used with a nut (not shown) to secure the detector sensor 56 to the module frame 52.

While not shown in FIGS. 10A and 10B, it is recognized that the module frame 52 includes features thereon for aligning and mating the frame 52 with the rails 17 (FIG. 3) of detector assembly 18. That is, as shown and described above in FIG. 8, the module frame 52 includes a rail datum location hole 110 that mates with a corresponding feature on the rail 17, such that the frame of detector module 20 is self-aligned with the rails 17. A mating feature 112 is also provided on module frame 52 for securing the frame to the rails 17.

Beneficially, the inclusion of a vertical or horizontal mounting structure 84, 114 on detector sensors 56—specifically of the alignment plate 86, 116 and datum alignment pins 88, 122 thereon—and of a module frame 52 with matching keyed features/datum holes 102, 104 for receiving the alignment pins, provides for self-aligning detector sensors 56 for a detector module 20. Removal and replacement of the detector sensors 56 is enabled without the aid of a precision fixture or highly skilled technician—such that a self-aligning detector sensor 56 can be removed and installed easily without special tools in a test bay, gantry test suite, or field. Additionally, single detector sensor 56 swapping and testing is enabled (instead of full, multi-detector sensor module swapping) via the mounting structure 84, 114 and module frame 52 design, so as to enable true plug-and-play capability and present time and cost savings—while still providing for precision alignment of single detector sensors.

Figure 11:
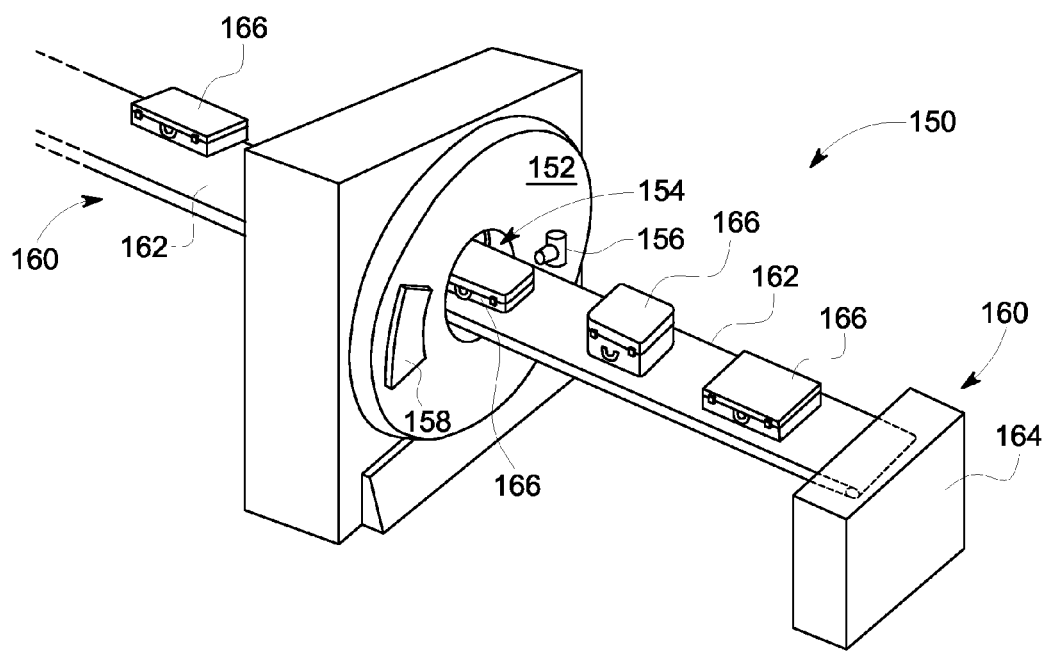
FIG. 11 is a pictorial view of a CT system for use with a non-invasive package inspection system.

Referring now to FIG. 11, construction of a detector module 20 is shown according to another embodiment of the invention. The detector module 20 includes a module frame 142 having a top surface 144 constructed to have a stepped configuration and thus includes a plurality of facets 146 thereon. The facets 146 are aligned lengthwise along the module frame 142, along the Z-axis, with each facet 146 being sized and configured to accommodate a detector sensor 56 to receive and process x-rays that attenuate through a patient or object. According to one embodiment of the invention, eight facets 146 are formed on the top surface 144 of module frame 142, with a detector sensor 56 positioned on each facet 146, such that the summation of each 32×16 array of detector elements in each detector sensor 56 results in an array size of 256×16 of detector elements for detector module 20. As a result, detector module 20 provides for 256 simultaneous slices of data to be collected with each rotation of gantry 12 (FIG. 1).

Referring now to FIG. 11, a package/baggage inspection system 150 is shown that includes a rotatable gantry 152 having an opening 154 therein through which packages or pieces of baggage may pass. The rotatable gantry 152 houses a high frequency electromagnetic energy source 106 as well as a detector assembly 158 having detector modules 20 similar to that shown in FIGS. 4-10. A conveyor system 160 is also provided and includes a conveyor belt 162 supported by structure 164 to automatically and continuously pass packages or baggage pieces 166 through opening 154 to be scanned. Objects 166 are fed through opening 154 by conveyor belt 162, imaging data is then acquired, and the conveyor belt 162 removes the packages 166 from opening 154 in a controlled and continuous manner. As a result, postal inspectors, baggage handlers, and other security personnel may non-invasively inspect the contents of packages 166 for explosives, knives, guns, contraband, etc.

According to an embodiment of the invention, incorporation of detector modules 20 (FIGS. 4-10) into the package/baggage inspection system 150 provides for decreased scanning time of packages 166. That is, detector modules 20 (FIGS. 4-10) allow for system 150 to scan a greater volume of the packages in a single revolution of gantry 152, as 256 slices can be acquired by detector modules 20. A more efficient scanning of packages 166 by package/baggage inspection system 150 is thus accomplished by way of detector modules 20 (FIGS. 4-10) being incorporated into the system 150.

Therefore, according to one embodiment of the invention, a CT system includes a rotatable gantry having an opening to receive an object to be scanned, an x-ray projection source positioned on the rotatable gantry that projects a beam of x-rays toward the object, and a plurality of detector modules positioned on the rotatable gantry and configured to receive x-rays attenuated by the object. Each of the plurality of detector modules further includes a module frame having a top surface and side surfaces thereon and a plurality of tileable detector sensors positioned on the top surface of the module frame so as to receive the x-rays attenuated by the object, with each of the plurality of tileable detector sensors including an array of detector elements configured to receive x-rays attenuated through the object and convert the x-rays into electrical signals and a mounting structure directly or indirectly coupled to the array of detector elements and configured to provide for a mounting and alignment of the detector sensor to the module frame, the mounting structure comprising an alignment plate positioned on the detector sensor on a surface thereof generally opposite the array of detector elements. The alignment plate includes alignment pins forming a datum structure to align the detector sensor on the module frame and one or more threaded bosses configured to receive a fastener therein that secures the detector sensor to the module frame. The module frame includes keyed features formed therein that receive the alignment pins of each respective detector sensor therein when the detector sensors are mounted on the module frame, so as to align the detector sensors on the module frame.

According to another embodiment of the invention, a detector module for receiving x-rays attenuated by an object during a CT scan procedure includes a module frame comprising a top surface and side surfaces, and a plurality of tileable detector sensors positioned on the module frame to receive the x-rays attenuated by the object. Each of the plurality of detector sensors further includes an array of detector pixels configured to receive x-rays attenuated through the object and convert the x-rays into electrical signals and an alignment plate directly or indirectly coupled to the array of detector elements on a side thereof opposite from which the x-rays are received, with the alignment plate having alignment pins forming a datum structure to align the detector sensor on the module frame and one or more threaded bosses configured to receive a fastener therein that secures the detector sensor to the module frame. The module frame includes datum holes formed therein that receive the alignment pins of each respective detector sensor therein when the detector sensors are mounted on the module frame, so as to align the detector sensors on the module frame.

According to yet another embodiment of the invention, a detector module for receiving x-rays attenuated by an object during a CT scan procedure includes a module frame and a plurality of selectively addable detector sensors positioned on the top surface of the module frame so as to receive the x-rays attenuated by the object. Each of the plurality of detector sensors further includes an array of detector elements configured to receive x-rays attenuated through the object and convert the x-rays into electrical signals and an alignment plate positioned on the detector sensor on a surface thereof generally opposite the array of detector elements, the alignment plate including alignment pins forming a datum structure to align the detector sensor on the module frame. The module frame includes datum holes formed therein that receive the alignment pins of each respective detector sensor therein when the detector sensors are mounted on the module frame, so as to align the detector sensors on the module frame.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A CT system comprising:
a rotatable gantry having an opening to receive an object to be scanned;
an x-ray projection source positioned on the rotatable gantry that projects a beam of x-rays toward the object; and
a plurality of detector modules positioned on the rotatable gantry and configured to receive x-rays attenuated by the object, each of the plurality of detector modules comprising:
a module frame having a top surface and side surfaces thereon; and
a plurality of tileable detector sensors positioned on the top surface of the module frame so as to receive the x-rays attenuated by the object;
wherein each of the plurality of tileable detector sensors comprises:
a substrate layer having a first surface and a second surface opposite the first surface;
an array of detector elements configured to receive x-rays attenuated through the object and convert the x-rays into electrical signals, wherein the array of detector elements is disposed on the first surface of the substrate layer; and
a mounting structure directly or indirectly coupled to the array of detector elements and configured to provide for a mounting and alignment of the detector sensor to the module frame, wherein the mounting structure comprises:
an alignment plate positioned on the detector sensor on the second surface of the substrate layer opposite the array of detector elements, wherein the alignment plate comprises:
alignment pins forming a datum structure to align the detector sensor on the module frame; and
one or more threaded bosses configured to receive a fastener therein that secures the detector sensor to the module frame; and
a thermal gap pad positioned between the alignment plate and the top surface and the side surface of the module frame to which the detector sensor is secured, the thermal gap pad being positioned in a recessed pocket formed in the alignment plate and comprising a thermal interface material (TIM) that provides a consistent low variation thermal interface with low thermal resistance between the detector sensor and the module frame, wherein the alignment plate of the mounting structure is disposed between the substrate layer and the thermal gap pad;
wherein the module frame includes keyed features formed therein that receive the alignment pins of each respective detector sensor therein when the detector sensors are mounted on the module frame, so as to align the detector sensors on the module frame.

2. The CT system of claim 1 wherein the substrate layer comprises an electrically insulating application specific integrated circuit (ASIC) package substrate layer, and wherein each of the plurality of detector modules further comprises: ASIC electronics package electrically and mechanically coupled to the array of detector elements to receive the analog electrical signals and convert the analog electrical signals to digital signals; and the electrically insulating ASIC package substrate layer positioned on a back surface of the ASIC electronics package opposite from the array of detector elements; wherein the alignment plate of the mounting structure is affixed directly to the electrically insulating ASIC package substrate layer.

3. The CT system of claim 1 wherein the keyed features of the module frame are formed in the top surface of the module frame, and wherein the module frame further comprises threaded openings formed through the module frame that extend out to the top surface of the module frame, with the threaded openings configured to receive fasteners that secure the detector sensors to the module frame.

4. The CT system of claim 3 wherein, for each detector sensor, the mounting structure comprises a vertical mounting structure where the alignment plate has a generally planar construction that is oriented parallel to the array of detector elements, such that the alignment pins of the alignment plate are received in respective keyed features formed in the top surface of the module frame and such that the one or more threaded bosses receive a fastener positioned through a respective threaded opening in the module frame, so as to align and secure the detector sensor on the module frame.

5. The CT system of claim 1 wherein the keyed features of the module frame are formed in one of the side surfaces of the module frame, and wherein the module frame further comprises threaded openings formed in the module frame that extend out to one side surface of the module frame, with the threaded openings configured to receive fasteners that secure the detector sensors to the module frame.

6. The CT system of claim 1 wherein each of the plurality of tileable detector sensors is selectively addable to the module frame to vary an amount of coverage of the detector module along the Z-axis, with the mounting structure of each respective detector sensor aligning the detector sensors on the module frame so as to provide a plug-and-play capability for each detector sensor.

7. The CT system of claim 1 wherein the module frame comprises alignment features configured to align and mate the module frame to a rail structure affixed on the rotatable gantry.

8. The CT system of claim 1 wherein the alignment pins and the one or more threaded bosses of the alignment plate are positioned on a surface of the alignment plate opposite the second surface of the substrate layer and within an outer perimeter of the array of detector elements.

9. A detector module for receiving x-rays attenuated by an object during a CT scan procedure, the detector module comprising:
a module frame comprising a top surface and side surfaces; and
a plurality of tileable detector sensors positioned on the module frame to receive the x-rays attenuated by the object, wherein each of the plurality of detector sensors comprises:
a substrate layer having a first surface and a second surface opposite the first surface;
an array of detector pixels configured to receive x-rays attenuated through the object and convert the x-rays into electrical signals, wherein the array of detector elements is disposed on the first surface of the substrate layer;
an alignment plate directly or indirectly coupled to the array of detector elements and positioned on the second surface of the substrate layer opposite the array of detector pixels, the alignment plate including:

alignment pins forming a datum structure to align the detector sensor on the module frame; and one or more threaded bosses configured to receive a fastener therein that secures the detector sensor to the module frame; and a thermal gap pad positioned in a recessed pocket formed in the alignment plate such that the thermal gap pad is compressed between the alignment plate and the module frame when the detector sensor is secured to the module frame, the thermal gap pad comprising a thermal interface material (TIM) that provides a consistent low variation thermal interface with low thermal resistance between the detector sensor and the module frame, wherein the alignment plate is disposed between the substrate layer and the thermal gap pad;

wherein the module frame includes datum holes formed therein that receive the alignment pins of each respective detector sensor therein when the detector sensors are mounted on the module frame, so as to align the detector sensors on the module frame.

10. The detector module of claim 9 wherein the alignment plate comprises a generally planar alignment plate that is oriented parallel to the array of detector elements and is directly or indirectly coupled thereto, with the alignment pins and a single threaded boss being formed on the generally planar alignment plate; and wherein the alignment pins of the generally planar alignment plate are received in respective datum holes formed in the top surface of the module frame and the single threaded boss of the generally planar alignment plate receives a fastener positioned through a respective threaded opening formed in the module frame and that extends out the top surface thereof, so as to align and secure the detector sensor on the module frame.

11. The detector module of claim 9 wherein each of the plurality of tileable detector sensors further comprises:

an application specific integrated circuit (ASIC) electronics package electrically and mechanically coupled to the array of detector pixels to receive analog electrical signals and convert the analog electrical signals to digital numbers;

a digital flex circuit connected to the ASIC electronics package to receive the digital signals therefrom and transfer the digital signals to an electronics board of the detector module; and the substrate layer positioned on a back surface of the ASIC electronics package opposite from the array of detector pixels to provide support to the detector sensor, and wherein the alignment plate is directly coupled to the substrate layer.

12. The detector module of claim 9 wherein the alignment pins and the one or more threaded bosses of the alignment plate are positioned within an x-ray collection area of the detector sensor defined by the array of detector pixels that receive x-rays attenuated through the object, the alignment pins being positioned on the detector sensor on a side thereof opposite from which the x-rays are received so as to be hidden on the detector sensor.

13. A detector module for receiving x-rays attenuated by an object during a CT scan procedure, the detector module comprising:

a module frame; and a plurality of selectively addable detector sensors positioned on the top surface of the module frame so as to receive the x-rays attenuated by the object;

wherein each of the plurality of detector sensors comprises:

a substrate layer having a first surface and a second surface opposite the first surface;

an array of detector elements configured to receive x-rays attenuated through the object and convert the x-rays into electrical signals, wherein the array of detector elements is disposed on the first surface of the substrate layer;

an alignment plate positioned on the detector sensor on the second surface of the substrate layer opposite the array of detector elements, the alignment plate including alignment pins forming a datum structure to align the detector sensor on the module frame; and a thermal gap pad positioned in a recessed pocket formed in the alignment plate such that the thermal gap pad is compressed between the alignment plate and the module frame when the detector sensor is secured to the module frame, the thermal gap pad comprising a thermal interface material (TIM) that provides a consistent low variation thermal interface with low thermal resistance between the detector sensor and the module frame, wherein the alignment plate is disposed between the substrate layer and the thermal gap pad;

wherein the module frame includes datum holes formed therein that receive the alignment pins of each respective detector sensor therein when the detector sensors are mounted on the module frame, so as to align the detector sensors on the module frame.

14. The detector module of claim 13 wherein the alignment plate comprises a generally planar alignment plate that is oriented parallel to the array of detector elements and is directly or indirectly coupled thereto, with the alignment pins and a single threaded boss being formed on the generally planar alignment plate; and wherein the alignment pins of the generally planar alignment plate are received in respective datum holes formed in the top surface of the module frame and the single threaded boss of the generally planar alignment plate receives a fastener positioned through a respective threaded opening formed in the module frame and that extends out the top surface thereof, so as to align and secure the detector sensor on the module frame.

* * * * *